United States Patent [19]

Magee

[11] 4,321,080
[45] Mar. 23, 1982

[54] ALGICIDAL AND FUNGICIDAL 1-HALO-2-SUBSTITUTED-THIOETHYL SULFONES, 2-SUBSTITUTED-THIOVINYL SULFONES, AND 1,2-DIHALOTHIOETHYL SULFONES

[75] Inventor: Philip S. Magee, Vallejo, Calif.

[73] Assignee: Chevron Research Company, San Francisco, Calif.

[21] Appl. No.: 176,898

[22] Filed: Aug. 11, 1980

Related U.S. Application Data

[60] Division of Ser. No. 60,114, Jul. 23, 1979, Pat. No. 4,255,451, which is a division of Ser. No. 912,778, Jul. 23, 1979, Pat. No. 4,196,152, which is a continuation-in-part of Ser. No. 814,013, Jul. 7, 1977, abandoned, which is a continuation-in-part of Ser. No. 657,677, Feb. 2, 1976, abandoned.

[51] Int. Cl.$^3$ ............................................. A01N 41/10
[52] U.S. Cl. .......................................... 71/67; 568/29
[58] Field of Search .............................. 71/67; 568/29

[56] References Cited

U.S. PATENT DOCUMENTS 3,984,481 10/1976 Magee .................................... 71/67
3,988,376 10/1976 Magee .................................... 71/67
4,031,247 6/1977 Magee .................................... 71/67

OTHER PUBLICATIONS

F. Montanari, Chem. Abstracts (1958), 52: 2790g & 2791b.
E. Prilezhaeva et al., N. D. Zelinskii Inst. Org. Chem., Acad. Sci. USSR, English Translation From Akad. Nauk SSSR, No. 7, pp. 1602–1608, (1970).

Primary Examiner—Mary C. Lee
Attorney, Agent, or Firm—D. A. Newell; T. G. DeJonghe; G. F. Swiss

[57] ABSTRACT

1-Halo-2-alkylthioethyl and 1-halo-2-arylthioethyl sulfones, having algicidal and fungicidal activity, are prepared by the addition of arylsulfenyl or alkylsulfenyl halides to alkyl or aryl vinyl sulfones. The thioethyl sulfone products are treated with a base to produce 2-alkylthiovinyl or 2-arylthiovinyl sulfones, which also have algicidal and fungicidal activity. The vinyl sulfones are halogenated to produce 1,2-dihalothioethyl sulfones, which have superior fungicidal activity, especially for tomato and celery late blight.

19 Claims, No Drawings

ALGICIDAL AND FUNGICIDAL 1-HALO-2-SUBSTITUTED-THIOETHYL SULFONES, 2-SUBSTITUTED-THIOVINYL SULFONES, AND 1,2-DIHALOTHIOETHYL SULFONES

RELATED APPLICATIONS

This is a division of application Ser. No. 60,114 filed July 23, 1979, now U.S. Pat. No. 4,255,451, which in turn is a division of application Ser. No. 912,778 filed July 23, 1979, now U.S. Pat. No. 4,196,152, which is a continuation-in-part of application Ser. No. 814,013, filed July 7, 1977 and now abandoned, which is a continuation-in-part of application Ser. No. 657,677, filed Feb. 2, 1976 and now abandoned.

BACKGROUND OF THE INVENTION

Shekhtman et al, *Chemical Abstract*, Vol. 76 (1972), pg. 58685n; Laba et al, *N. D. Zelinskii Inst. Org. Chem.*, USSR, No. 10, pp. 2149–2156 (1969); and *N. D. Zelinskii Inst. Org. Chem.*, USSR, No. 7, pp. 1602–1608 (1970) disclose the preparation of alkyl alkylthiovinyl sulfones by the addition of alkyl mercaptans to acetylenic sulfones.

Montarari et al, *Chemical Abstracts*, Vol. 51 (1957), pg. 5721f; Vol. 52 (1958), pg. 2790g; and Vol. 55 (1961), pg. 3494a, disclose the preparation of arylthiovinyl aryl sulfones. Prilezhaeva et al, *Chemical Abstracts*, Vol. 67 (1967), pg. 108135v and Vol. 68 (1968), pg. 59110t, disclose the preparation of beta-substituted ethyl vinyl sulfones by the addition of alcohols and mercaptans to divinyl sulfones.

U.S. Pat. No. 3,021,370, issued to Bluestone on Feb. 13, 1962, discloses polyunsaturated sulfides and sulfones, and U.S. Pat. No. 3,101,377, issued to Bluestone et al on Aug. 20, 1977, discloses sulfone derivatives of mercapto haloethylenes.

DESCRIPTION OF THE INVENTION

The 1-halo-2-substituted-thioethyl sulfones of the invention are represented by the formula,

the 2-substituted-thiovinyl sulfones of the invention are represented by the formula, $$RSO_2CH = CHSR^1 \qquad (II)$$

and the 1,2-dihalothioethyl sulfones of the invention are represented by the formula

wherein X is chloro or bromo, R and $R^1$ individually are alkyl of 1 to 6 carbon atoms, phenyl or phenyl substituted with 1 to 2 of the same or different substituents selected from fluoro, chloro, bromo, nitro or alkyl of 1 to 4 carbon atoms.

Representative alkyl R and $R^1$ groups are methyl, ethyl, isopropyl and hexyl. Representative aryl R and $R^1$ groups are 2-fluorophenyl, 4-chlorophenyl, 3,5-dibromophenyl, 2-nitro-4-methylphenyl, 4-tolyl and 2-chloro-4-methylphenyl.

Preferred aryl R or $R^1$ groups are phenyl or phenyl substituted with 1 to 2 of the same or different substituents selected from fluoro, chloro or bromo. Preferred alkyl R or $R^1$ groups are alkyl of 1 to 3 carbon atoms.

In part due to their superior fungicidal activity, preferred classes of compounds represented by formulas (I), (II) and (III) are those wherein one R or $R^1$ group is alkyl of 1 to 6 carbon atoms and the other R or $R^1$ group is phenyl or phenyl substituted with 1 to 2 of the same or different substituents selected from fluoro, chloro, bromo, nitro or alkyl of 1 to 4 carbon atoms. In this class, most preferably one R or $R^1$ group is alkyl of 1 to 6 carbon atoms and the other R or $R^1$ group is phenyl or phenyl substituted with 1 to 2 fluoro, chloro or bromo.

A particularly preferred class of 1,2-dihalothioethyl sulfones of formula (III) is that wherein R and $R^1$ is as defined in the preceding paragraph and both X are bromo.

Representative compounds of the invention include:
methyl 1-chloro-2-methylthioethyl sulfone,
ethyl 1-bromo-2-hexylthioethyl sulfone,
methyl 1-chloro-2-p-bromophenylthioethyl sulfone,
hexyl 1-chloro-2-o-nitrophenylthioethyl sulfone,
ethyl 1-bromo-2-o-fluorophenylthioethyl sulfone,
methyl 2-methylthiovinyl sulfone,
ethyl 2-o-chlorophenylthiovinyl sulfone,
hexyl 2-(2-methyl-4-chlorophenylthio)vinyl sulfone,
ethyl 2-(2-bromo-4-chlorophenylthio)vinyl sulfone,
p-chlorophenyl 1-chloro-2-p-chlorophenylthioethyl sulfone,
o-tolyl 2-o-tolylsulfone,
p-nitrophenyl 2-p-tolylthiovinyl sulfone,
ethyl 1,2-dibromothioethyl sulfone,
methyl 1,2-dibromo-2-p-nitrophenylthioethyl sulfone, and
p-chlorophenyl 1,2-dibromo-2-phenylthioethyl sulfone.

The 1-halo-2-substituted-thioethyl sulfones (I) are prepared by adding a sulfenyl halide (III) to a vinyl sulfone (IV) and the 2-substituted-thiovinyl sulfones (II), are prepared by dehydrohalogenating the 1-halo-2-substituted-thioethyl sulfones (I) with a base, as depicted in the following reactions:

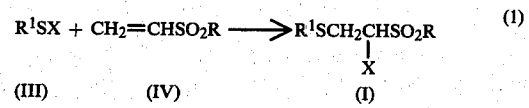

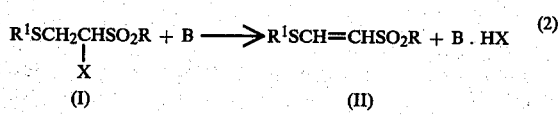

wherein R, $R^1$ and X have the same significance as previously defined and B is a base.

Reaction (1) is conducted by reacting substantially equimolar amounts of the sulfenyl halide (III) and the vinyl sulfone (IV) in the liquid phase at a temperature of about 0° to 100° C. Generally, an inert organic solvent, such as an alkane, a haloalkane or an aromatic compound, is employed in the reaction. Reaction pressure is suitably atmospheric, subatmospheric or superatmospheric. For convenience, the reaction pressure is generally atmospheric. The reaction is generally exothermic and is completed in about 1 to 24 hours. The 1-halo-2- substituted-thioethyl sulfone product (I) is isolated and purified by conventional procedures such as extraction, filtration, chromatography, distillation, or alternatively, is used directly in reaction (2) without purification and/or isolation.

In reaction (2), the 1-halo-2-substituted-thioethyl sulfone (I) is treated with substantially equimolar amounts of an inorganic or organic base. The preferred base is an organic base such as a pyridine compound, e.g., pyridine or an alkylpyridine, or a trialkylamine, e.g., triethylamine. Reaction (2) is conducted in the liquid phase at a temperature of 0° to 100° C. Generally, an inert organic diluent such as a haloalkane, e.g., dichloromethane or an aromatic hydrocarbon, e.g., benzene, is employed in the reaction. The reaction pressure is not critical, and, for convenience, the pressure is generally atmospheric. The reaction is generally complete within about 1 to 24 hours. The product (II) is isolated and purified by conventional procedures such as filtration, extraction, distillation, chromatography, etc.

The 1,2-dihalothioethyl sulfones (IV) are prepared by the addition of halogen to the 2-substituted-thiovinyl sulfone (II) by conventional procedures. Alternatively, the 1,2-dihalothioethyl sulfones (III) can be prepared by halogenating the 2-substituted-thiovinyl sulfone with sulfuryl halide, e.g., sulfuryl chloride, by conventional procedures.

UTILITY

The compounds of the invention are useful for controlling fungi, particularly plant fungal infections caused by *Botrytis cinerea*, leaf blights caused by organisms such as *Pythrium ultimum, Helminthosporum sativum, Fusarium moniliforme, Rhizoctonia solani, Monolinia fructicola* and *Uromyces phaseoli typica*. However, some fungicidal compounds of the invention may be more fungicially active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. There compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

The compounds of the invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, steams, canals, pools and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep 0.1 to 10 ppm is equal to about 0.3 to 30 pounds per acre of water one foot deep. These compounds may be applied to the aqueous growth environments of such organisms as dispersible powders or in solution with water-miscible solvents.

EXAMPLE 1

Preparation of ethyl 2-(4-chlorophenylthio) vinyl sulfone 4-chlorophenylsulfenyl chloride, 7.5 g was added to 5.0 g of ethyl vinyl sulfone in 20 ml of dichloromethane. There was no exotherm and the system was refluxed for 3 hours. The dichloromethane was removed by stripping and the residue was dissolved in 50 ml of benzene. Triethylamine, 4.2 g, was added dropwise with cooling and after standing for 1 hour, the triethylamine hydrochloride was removed by filtration and the benzene stripped to give a crude product. Purification was carried out by chromatography on a silica gel column. The product, ethyl 2-(4-chlorophenylthio)vinyl sulfone, 4.2 g, was obtained as a clear oil showing one spot by thin-layer chromatography.

Examination by infrared and NMR spectroscopy was in complete accord with the proposed structure. The product is tabulated in Table I as Compound No. 1.

EXAMPLE 2

Preparation of ethyl 2-(4-nitrophenylthio)vinyl sulfone

Ten grams of 4-nitrophenylsulfenyl chloride was combined with 6.4 g of ethyl vinyl sulfone in 30 ml of dichloromethane and refluxed for 6 hours. Stripping and reaction with triethylamine in benzene initially gave a crude red oil which crystallized on standing, m.p. 55°-58° C.

The NMR spectrum fully supports the structure for ethyl 2-(4-nitrophenylthio)vinyl sulfone. The product and its elemental analysis is tabulated in Table I as Compound No. 2.

EXAMPLE 3

Preparation of ethyl 1-chloro-2-p-chlorophenylthioethyl sulfone

Five grams of 4-chlorophenylsulfenyl chloride was refluxed with 3.3 g ethyl vinyl sulfone for 3 hours in 20 ml of dichloromethane. The stripped product showed 3 spots by thin layer chromatography and was purified by chromatography over silica gel. The purified product eluted with dichloromethane and solidified after stripping to a white solid, 6.4 g, m.p. 60°-62° C.

The product and its elemental analysis are tabulated in Table II as Compound No. 24.

EXAMPLE 4

Preparation of ethyl methylthiovinyl sulfone

A 25.0-g (0.185-mol) sample of sulfuryl chloride was added dropwise to 15.0 g (0.159 mol) methyl disulfide at a temperature of −20° C. The reaction mixture was evaporated under reduced pressure to give methyl sulfenyl chloride.

A solution of 6.0 g methyl sulfenyl chloride, 10 g (0.083 mol) ethyl vinyl sulfone and 20 ml dichloromethane was contacted at ambient temperature (exothermic reaction) and warmed with a sunlamp for 1 hour. The resulting reaction mixture was evaporated under reduced pressure and the residue was chromatographed on a silica gel column (dichloromethane/hexane eluants). A 6.1-g sample of ethyl 1-chloro-2-methylthioethyl sulfone was eluted from the column with dichloromethane. The nuclear magnetic resonance spectrum of the product was consistent with the molecular structure.

A solution of 6.1 g (0.03 mol) ethyl 1-chloro-2-methylthioethyl sulfone and 3.3 g (0.032 mol) triethylamine in 30 ml benzene was contacted at ambient temperature. A heavy precipitate of triethylamine hydrochloride was formed. The reaction mixture was filtered and evaporated under reduced pressure to give 4.8 g of ethyl methylthiovinyl sulfone. The product is tabulated in Tabel I as Compound No. 9.

EXAMPLE 5

Preparation of phenyl 2-(4-bromophenylthio)ethyl sulfone

A solution of 6.7 g of 4-bromophenylsulfenyl chloride and 5.0 g of phenyl vinyl sulfone in 30 ml of dichloromethane was refluxed for 5 hours. The solvent was stripped and the residue dissolved in 40 ml of benzene. This solution was cooled in ice and treated with 3.1 g triethylamine. After filtering and stripping, the crude product showed four components by thin-layer chromatography. Column chromatography over silica gave 5.6 g of the pure thiovinyl sulfone product, m.p. 53°-58° C. The product and its elemental analysis are tabulated in Table I as Compound No. 17.

EXAMPLE 6

Preparation of phenyl 1,2-dibromo-2-(p-bromophenylthio)ethyl sulfone

Four grams of bromine were added to a solution of 6.0 grams of phenyl 2-(4-bromophenylthio)vinyl sulfone in 30 ml of acetic acid. Bromination was rapid with separation of the dibromide. The slurry was poured into ice water to complete the precipitation. The product was separated, washed with water and dried in air giving 10.0 grams (100%) of the pure dibromide; m.p. 133°-135° C.

The product is tabulated in Table II as Compound No. 27.

EXAMPLE 7

Preparation of ethyl 1,2-dibromo-2-(4-chlorophenylthio)ethyl sulfone

Three grams of bromine were added to a solution of 4.5 grams of ethyl 2-(4-chlorophenylthio)vinyl sulfone in 20 ml of acetic acid. After stirring at room temperature for one hour, the solution was poured into 400 ml of ice water, causing separation of an oil. The product was dissolved in 100 ml of dichloromethane, then washed once with aqueous sodium carbonate, twice with water and dried over magnesium sulfate. Filtering and solvent removal gave 7.0 grams of the dibromide product, as a thick oil. The product is tabulated in Table II as Compound No. 29.

The compounds tabuated in Table I were prepared by procedures similar to that of Examples 1-7. The structure of each compound tabulated in Table I was confirmed by nuclear magnetic resonance and/or infrared spectroscopy.

EXAMPLE 8

Mycelial Inhibition

A number of the compounds of the present invention were evaluated for in vitro fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were inoculated with the particular mycelium growth by covering the paper with a potato dextrose broth culture of mycelial suspension. The inoculated papers were then placed on potato dextrose agar plates and sprayed by means of a micro sprayer with the fungicidal solution. The treated paper strips were incubated at 25° C. and data is taken after 24 hours. Fungicidal activities are measured by a zone of inhibited mycelial growth from the center of the paper strip. The effectiveness of the compounds tests for fungicidal activity is reported in Table III in terms of the microgram/cm$^2$ for 99% control of the fungus.

EXAMPLE 9

Alga Control

Representative compounds of the invention were tested as algicides by the following method. The alga test species were Lemna, Elodea, and Spirolina.

An acetone solution of the test compound and a small amount of an alkylarylpolyoxyethylene glycol-containing surfactant was prepared. This solution was mixed with a nutrient broth in a quantity sufficient to give a conentration of 2 ppm. A 240-ml container was filled with this mixture. A sample of the test alga was added to each container and the container was then placed in an illuminated environment maintained at a temperature of about 20° C. for incubation. The containers were observed periodically for alga growth (as compared to an untreated check). The algicidal effectiveness of the test compound was determined based on a final observation of alga growth after 7 to 10 days. The results of the test on a 0-to-100 basis—0 indicating no effectiveness and 100 indicating complete effectiveness—are reported in Table IV.

EXAMPLE 10

Tomato Late Blight

Compounds of the invention were tested for the control of the Tomato Late Blight organism *Phytophthora infestans conidia*. Five- to six-week-old tomato (variety Bonny Best) seedlings were used. The tomato plants were sprayed with a 250-ppm solution of the test compound in acetone, water and a small amount of a non-ionic emulsifier. The sprayed plants were then inoculated one day later with the organism, placed in an environmental chamber and incubated at 66°–68° F. and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants. The compounds giving effective control at the test concentration are tabulated in Table II.

EXAMPLE 11

Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compounds giving effective control at the test concentration are tabulated in Table V.

EXAMPLE 12

Celery Late Blight

Compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a non-ionic emulsifier. The plants were then inoculated with the organism and placed in an environmental chamber and incubated at 66°–68° F. in 100% relative humidity for an extended period of time (approximately 48 hours). Following the incubation, the plants were allowed to dry and then were maintained at a 60–80% relative humidity for approximately 14 days. The percent disease control provided by a given candidate toxicant is based on the percent disease reduction relative to untreated check plants. The compounds giving effective control at the test concentrations are reported in Table V.

TABLE I

Compounds of the Formula $RSO_2CH=CHSR^1$

| Compound No. | R | $R^1$ | Physical State | Sulfur Calc. | Sulfur Found | Halogen Calc. | Halogen Found |
|---|---|---|---|---|---|---|---|
| 1 | $C_2H_5$ | p-Cl—φ | Liquid | 24.4 | 24.5 | 13.5 | 12.7 |
| 2 | $C_2H_5$ | p-NO$_2$—φ | m.p. 55–58° C. | 23.4 | 22.6 | — | — |
| 3 | $C_2H_5$ | 3,4-Cl$_2$—φ | Oil | 21.5 | 21.7 | 23.8 | 25.0 |
| 4 | $C_2H_5$ | p-CH$_3$—φ | Liquid | 26.5 | 26.0 | — | — |
| 5 | $CH_3$ | p-Cl—φ | Liquid | 25.8 | 25.4 | 14.3 | 15.2 |
| 6 | $CH_3$ | 2,5-Cl$_2$—φ | m.p. 107–109° C. | 22.6 | 22.4 | 25.0 | 25.6 |
| 7 | $CH_3$ | p-Br—φ | Liquid | 21.9 | 21.3 | 27.3 | 25.9 |
| 8 | $C_2H_5$ | p-Br—φ | Liquid | 20.9 | 20.6 | 26.0 | 29.3 |
| 9 | $C_2H_5$ | $CH_3$ | Liquid | 38.5 | 38.3 | — | — |
| 10 | φ | p-Cl—φ | Liquid | 20.6 | 20.8 | 11.4 | 11.7 |
| 11 | p-Cl—φ | p-Cl—φ | m.p. 77–79° C. | 18.6 | 18.8 | 20.5 | 20.3 |
| 12 | φ | 3,4-Cl$_2$—φ | m.p. 60–62° C. | 18.6 | 18.5 | 20.5 | 21.8 |
| 13 | p-Cl—φ | $CH_3$ | m.p. 72–74° C. | 25.8 | 25.8 | 14.3 | 16.5 |

TABLE I-continued
Compounds of the Formula $RSO_2CH=CHSR^1$

| Compound No. | R | $R^1$ | Physical State | Sulfur Calc. | Sulfur Found | Halogen Calc. | Halogen Found |
|---|---|---|---|---|---|---|---|
| 14 | p-Cl—φ | $C_2H_5$ | Liquid | 24.4 | 23.8 | 13.5 | 14.5 |
| 15 | φ | $C_2H_5$ | Liquid | 28.1 | 27.1 | — | — |
| 16 | $C_2H_5$ | 2,5-$Cl_2$—φ | Liquid | 21.6 | 20.9 | 23.9 | 24.1 |
| 17 | φ | p-Br—φ | m.p. 53–58° C. | 18.1 | 18.1 | 22.5 | 21.8 |

TABLE II
Compounds of the Formula $RSO_2\underset{X^1}{CH}\underset{X^2}{CHSR^1}$

| Compound No. | R | $X^1$ | $X^2$ | $R^1$ | Melting Point, °C. | Sulfur Calc. | Sulfur Found | Halogen Calc. | Halogen Found |
|---|---|---|---|---|---|---|---|---|---|
| 18 | $CH_3$ | Cl | H | 3,4-$Cl_2$—φ | Oil | 20.1 | 20.8 | 33.3 | 30.9 |
| 19 | $C_2H_5$ | Cl | H | 3,4-$Cl_2$—φ | Oil | 19.2 | 19.1 | 31.9 | 32.2 |
| 20 | $CH_3$ | Cl | H | p-F—φ | 48–50 | 33.9 | 24.1 | 13.2 (Cl) | 14.2 |
| 21 | $C_2H_5$ | Cl | H | p-F—φ | Oil | 22.7 | 22.9 | 12.5 (Cl) | 14.2 |
| 22 | φ | Cl | H | p-Cl—φ | 80–82 | 18.5 | 17.0 | 20.4 | 21.1 |
| 23 | $CH_3$ | Cl | H | p-Cl—φ | 83–85 | 22.5 | 22.5 | 24.9 | 24.9 |
| 24 | $C_2H_5$ | Cl | H | p-Cl—φ | 60–62 | 21.4 | 21.9 | 23.7 | 23.2 |
| 25 | φ | Br | Br | p-Br—φ | 133–135 | 12.5 | 12.4 | 46.5 | 46.3 |
| 26 | $C_2H_5$ | Br | Br | p-Cl—φ | Oil | 15.2 | 14.6 | 7.1 | 7.6 |
| 27 | $CH_3$ | Br | Br | 2,5-$Cl_2$—φ | 78–80 | 14.5 | 14.2 | 9.0 | 9.1 |
| 28 | $CH_3$ | Br | Br | 3,4-$Cl_2$—φ | Oil | 14.5 | 13.8 | 9.0 | 9.0 |
| 29 | $C_2H_5$ | Br | Br | 3,4-$Cl_2$—φ | Oil | 14.0 | 13.9 | 8.7 | 9.6 |
| 30 | $CH_3$ | Br | Br | p-F—φ | Oil | 16.4 | 16.6 | 40.8 (Br) | 39.2 |
| 31 | $C_2H_5$ | Br | Br | p-F—φ | Oil | 15.8 | 16.1 | 39.3 (Br) | 43.9 |
| 32 | φ | Br | Br | p-Cl—φ | 118–119 | 13.6 | 13.6 | 6.3 | 6.3 |
| 33 | $CH_3$ | Br | Br | p-Cl—φ | 58–60 | 15.7 | 13.2 | 7.3 | 5.9 |
| 34 | $CH_3$ | Br | Br | p-Br—φ | 75–77 | 14.2 | 13.3 | 52.9 | 45.2 |
| 35 | $C_2H_5$ | Br | Br | p-Br—φ | 89–90 | 13.7 | 13.6 | 51.3 | 47.0 |
| 36 | $C_2H_5$ | Br | Br | 3,4-$Cl_2$—φ | Oil | 14.0 | 13.5 | 8.7 | 8.0 |
| 37 | $CH_3$ | Cl | Cl | p-Cl—φ | 68–70 | 20.1 | 20.1 | 33.3 | 32.6 |
| 38 | $CH_3$ | Cl | Cl | p-Br—φ | 88–90 | 17.6 | 16.6 | 8.2 | 7.7 |

TABLE III
Mycelia Inhibition, micrograms/$cm^2$ for 99% control

| Compound No. | (1) | (2) | (3) | (4) | (5) |
|---|---|---|---|---|---|
| 1 | 0.76 | 0.63 | 0.68 | 0.87 | 0.34 |
| 2 | 0.92 | 0.92 | 0.73 | >1.7 | 0.76 |
| 3 | 1.6 | 0.65 | 1.5 | 1.5 | 0.54 |
| 4 | >1.7 | 0.92 | 1.2 | 1.7 | 0.65 |
| 5 | 0.36 | 0.31 | 0.50 | 0.63 | — |
| 6 | 0.85 | 0.26 | 0.68 | 0.56 | — |
| 7 | 0.48 | 0.41 | 0.59 | 0.76 | — |
| 8 | 0.78 | 0.4 | 0.76 | 0.7 | — |
| 9 | >1.7 | >1.7 | >1.7 | >1.7 | >1.7 |
| 10 | >1.7 | 1.1 | >1.7 | >1.7 | 1.1 |
| 11 | >1.7 | 1.6 | >1.7 | >1.7 | >1.7 |
| 12 | >1.7 | 1.5 | >1.7 | >1.7 | >1.7 |
| 13 | >1.7 | >1.7 | >1.7 | 1.1 | 1.1 |
| 14 | >1.7 | 0.34 | 1.2 | 1.3 | 1.1 |
| 15 | >1.7 | 1.6 | 0.68 | >1.7 | >1.7 |
| 16 | 1.55 | 0.35 | 0.69 | 0.64 | 0.7 |
| 17 | >1.7 | 0.41 | >1.7 | 1.1 | — |
| 18 | >1.7 | >1.7 | >1.7 | >1.7 | >1.7 |
| 19 | — | — | — | — | — |
| 20 | — | 0.2 | 0.95 | 1.4 | — |
| 21 | — | 0.38 | 1.3 | >1.7 | — |
| 22 | — | — | >1.7 | >1.7 | >1.7 |
| 23 | — | — | >1.7 | 1.1 | >1.7 |
| 24 | >1.7 | 0.17 | 0.6 | 0.73 | — |
| A | >1.7 | >1.7 | >1.7 | >1.7 | >1.7 |
| B | >1.7 | >1.7 | >1.7 | >1.7 | >1.7 |

A = Ethyl 2-(p-chlorophenylthio)ethyl sulfone
B = Ethyl vinyl sulfone
(1) = *Pythium ultimum*
(2) = *Rhizoctonia solani*
(3) = *Aspergillus niger*
(4) = *Fusarium moniloforma*
(5) = *Botrytis cinerea*

TABLE IV
Percent Aquatic Weed Control

| Compound No. | Lemna | Elodea | Spirolina |
|---|---|---|---|
| 1 | 100 | 39 | 60 |
| 2 | 0 | 0 | 90 |
| 3 | 60 | 39 | 90 |
| 4 | 0 | >0 | 80 |
| 5 | 99 | 60 | 90 |
| 6 | 99 | 70 | 80 |
| 7 | 99 | 78 | 75 |
| 8 | 99 | 50 | 80 |
| 9 | 100 | 90 | 0 |
| 10 | 39 | 39 | 100 |
| 11 | 60 | 70 | 90 |
| 12 | 70 | 30 | 90 |
| 13 | 99 | 90 | 100 |
| 14 | 90 | 85 | 95 |
| 15 | 70 | 90 | 100 |
| 16 | 99 | 90 | 100 |
| 17 | 85 | 67 | 75 |
| 18 | 100 | 85 | 70 |

TABLE IV-continued

| Compound No. | Percent Aquatic Weed Control | | |
|---|---|---|---|
| | Lemna | Elodea | Spirolina |
| 19 | 70 | 90 | 80 |
| 20 | 95 | 90 | 100 |
| 21 | 80 | 90 | 100 |
| 22 | 60 | 70 | 40 |
| 23 | 100 | 100 | 100 |
| 24 | 90 | 78 | 90 |
| 25 | 0 | 0 | 30 |
| 26 | 65 | 60 | 40 |
| 27 | 80 | 80 | 0 |
| 28 | 85 | 65 | 0 |
| 29 | 40 | 60 | 90 |
| 30 | 70 | 90 | 100 |
| 31 | 60 | 70 | 95 |
| 32 | 0 | 0 | 60 |
| 33 | 100 | 100 | 95 |
| 34 | 0 | 0 | 30 |
| 35 | 85 | 80 | 90 |
| 36 | 0 | 0 | 70 |
| 37 | 70 | 80 | 0 |
| 38 | 70 | 95 | 0 |
| A | 0 | 0 | 0 |
| B | 0 | 0 | 70 |

A = Ethyl 2-(p-chlorophenylthio)ethyl sulfone
B = Ethyl vinyl sulfone

TABLE V

| Compound No. | % Control | | |
|---|---|---|---|
| | Tomato Late Blight | Celery Late Blight | Tomato Early Blight |
| 1 | 75 | 0 | 44 |
| 2 | — | 27 | 76 |
| 3 | — | — | — |
| 4 | 0 | 0 | 44 |
| 5 | 39 | — | 0 |
| 6 | 39 | — | 84 |
| 7 | 56 | — | 56 |
| 8 | 39 | — | 0 |
| 9 | 0 | 0 | 75 |
| 10 | 50 | 63 | 23 |
| 11 | 64 | 44 | 23 |
| 12 | 64 | 63 | 23 |
| 13 | 95 | 68 | 0 |
| 14 | 0 | 0 | 0 |
| 15 | 0 | 0 | 0 |
| 16 | 35 | 23 | 33 |
| 17 | 56 | — | 56 |
| 18 | — | 93 | — |
| 19 | — | 98 | 0 |
| 20 | — | 94 | — |
| 21 | — | 89 | — |
| 22 | — | — | 0 |
| 23 | — | — | 0 |
| 24 | 11 | — | 23 |
| 25 | 71 | 56 | 83 |
| 26 | 71 | 0 | 41 |
| 27 | 95 | 95 | 60 |
| 28 | 0 | 33 | 0 |
| 29 | — | — | — |
| 30 | — | 97 | — |
| 31 | — | 97 | — |
| 32 | — | — | 0 |
| 33 | — | 97 | 0 |
| 34 | — | 94 | — |
| 35 | 96 | 93 | 23 |
| 36 | — | 84 | — |

What is claimed is:

1. A method for the control of algae which comprises applying thereto an algicidally effective amount of a compound of the formula $$RSO_2CHCHSR^1$$
$$\phantom{RSO_2C}|\phantom{HC}|$$
$$\phantom{RSO_2CH}X\phantom{CH}X$$

wherein X is chloro or bromo, and one of R or $R^1$ is alkyl of 1 to 6 carbon atoms, and the other R or $R^1$ group is phenyl or phenyl substituted with 1 to 2 of the same or different substituents selected from fluoro, chloro, bromo, nitro or alkyl of 1 to 4 carbon atoms.

2. A method for the control of algae which comprises applying thereto an algicidally effective amount of a compound of the formula $$RSO_2CH-CH_2SR^1$$
$$\phantom{RSO_2C}|$$
$$\phantom{RSO_2CH}X$$

wherein X is chloro or bromo and one of R or $R^1$ is alkyl of 1 to 6 carbon atoms, and the other R or $R^1$ group is phenyl or phenyl substituted with 1 to 2 of the same or different substituents selected from fluoro, chloro, bromo, nitro or alkyl of 1 to 4 carbon atoms.

3. A method for the control of algae which comprises applying thereto an algicidally effective amount of a compound of the formula $$RSO_2CH=CHSR^1$$

wherein one of R or $R^1$ is alkyl of 1 to 6 carbon atoms, and the other R or $R^1$ group is phenyl or phenyl substituted with 1 to 2 of the same or different substituents selected from fluoro, chloro, bromo, nitro or alkyl of 1 to 4 carbon atoms.

4. The method of claim 1 wherein R is alkyl of 1 to 6 carbon atoms and $R^1$ is phenyl substituted with 1 to 2 of the same or different substituents selected from fluoro, chloro, bromo, nitro or alkyl of 1 to 4 carbon atoms.

5. The method of claim 4 wherein X is bromo, R is ethyl and $R^1$ is p-chlorophenyl.

6. The method of claim 4 wherein X is bromo, R is methyl and $R^1$ is 2,5-dichlorophenyl.

7. The method of claim 4 wherein X is bromo, R is methyl and $R^1$ is p-chlorophenyl.

8. The method of claim 4 wherein X is bromo, R is ethyl and $R^1$ is p-bromophenyl.

9. The method of claim 2 wherein R is alkyl of 1 to 6 carbon atoms and $R^1$ is phenyl substituted with 1 to 2 of the same or different substituents selected from fluoro, chloro, bromo, nitro or alkyl of 1 to 4 carbon atoms.

10. The method of claim 9 wherein X is chloro, R is methyl and $R^1$ is 3,4-dichlorophenyl.

11. The method of claim 9 wherein X is chloro, R is methyl and $R^1$ is p-fluorophenyl.

12. The method of claim 9 wherein X is chloro, R is ethyl and $R^1$ is p-fluorophenyl.

13. The method of claim 9 wherein X is chloro, R is methyl and $R^1$ is p-chlorophenyl.

14. The method of claim 3 wherein R is p-chlorophenyl and $R^1$ is methyl.

15. The method of claim 3 wherein R is alkyl of 1 to 6 carbon atoms and $R^1$ is phenyl substituted with 1 to 2 of the same or different substituents selected from fluoro, chloro, bromo, nitro or alkyl of 1 to 4 carbon atoms.

16. The method of claim 15 wherein R is methyl and $R^1$ is p-chlorophenyl.

17. The method of claim 15 wherein R is methyl and $R^1$ is 2,5-dichlorophenyl.

18. The method of claim 15 wherein R is ethyl and $R^1$ is 2,5-dichlorophenyl.

19. The method of claim 15 wherein R is methyl and $R^1$ is p-bromophenyl.

* * * * *